(12) United States Patent
Cobb

(10) Patent No.: US 12,274,695 B2
(45) Date of Patent: Apr. 15, 2025

(54) PHARMACEUTICAL DRUG THERAPY FOR AUTISM

(71) Applicant: Leland Cobb, Virginia Beach, VA (US)

(72) Inventor: Leland Cobb, Virginia Beach, VA (US)

( * ) Notice: Subject to any disclaimer, the term of this patent is extended or adjusted under 35 U.S.C. 154(b) by 161 days.

(21) Appl. No.: 17/393,471

(22) Filed: Aug. 4, 2021

(65) Prior Publication Data

US 2022/0087998 A1 Mar. 24, 2022

Related U.S. Application Data

(60) Provisional application No. 63/082,216, filed on Sep. 23, 2020.

(51) Int. Cl.
*A61K 31/465* (2006.01)
*A61K 31/137* (2006.01)
*A61K 31/40* (2006.01)
*A61P 25/00* (2006.01)

(52) U.S. Cl.
CPC .......... *A61K 31/465* (2013.01); *A61K 31/137* (2013.01); *A61K 31/40* (2013.01); *A61P 25/00* (2018.01)

(58) Field of Classification Search
CPC .... A61K 31/137; A61K 31/40; A61K 31/465; A61K 2300/00; A61P 25/00
See application file for complete search history.

(56) References Cited

FOREIGN PATENT DOCUMENTS

WO WO-2004075877 A1 * 9/2004 .......... A61K 31/135
WO WO-2019010254 A1 * 1/2019 ............. A23L 33/12

OTHER PUBLICATIONS

Jutkiewicz et. al., Psychopharmacology, vol. 200, pp. 93-103, publ. Jun. 20, 2008 (Year: 2008).*
Berman et. al., Molecular Psychiatry, vol. 14, pp. 123-142, publ. Aug. 12, 2008 (Year: 2008).*

* cited by examiner

*Primary Examiner* — Sarah Pihonak
(74) *Attorney, Agent, or Firm* — The Rapacke Law Group, P.A.; Andrew Rapacke

(57) ABSTRACT

A pharmaceutical drug therapy for autism is disclosed, including a sufficient amount of nicotine and a sufficient amount of amphetamine.

11 Claims, 1 Drawing Sheet

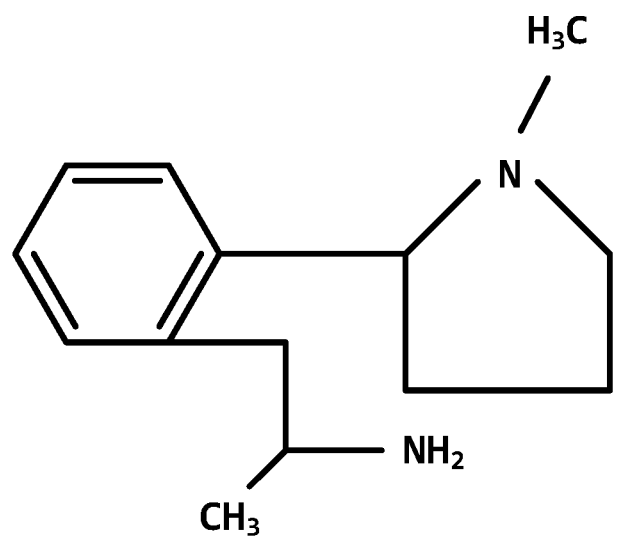

PHARMACEUTICAL DRUG THERAPY FOR AUTISM

CROSS-REFERENCE TO RELATED APPLICATIONS

The present application claims priority to U.S. Provisional Patent Application 63/082,216 filed on Sep. 23, 2020, entitled "PHARMACEUTICAL DRUG THERAPY FOR AUTISM" the entire disclosure of which is incorporated by reference herein.

TECHNICAL, FIELD

The present disclosure relates generally to the field of pharmaceutical drug therapy systems and methods. More specifically, the present disclosure relates to a pharmaceutical drug therapy for the treatment of autism.

BACKGROUND

Autism Spectrum disorder is a developmental disorder which is defined by the Centers for Disease Control and Prevention, as developmental disability which effects behavior, social, and communication. In the Diagnostic Criteria of the DSM-5 infers in Autistic individuals has defects in social emotional cooperation and exchange; Social approach and in continuous conversation. In addition, the abnormality's in sharing of emotions/interests and failure in identifying social ques and response to a not vocal behavior. Problems in understanding relationships, advancing relationships and maintaining.

The Spectrum of impairments are quantified by repetitive behaviors/patterns in daily life, and in repetitive movements. Moments of inflexibility to daily routines or exhibits extreme distress to small changes; certain episodes may cause aggression by changes in routine. May have intense interest/fixated focus on a certain topic or attachment. Hyperactivity to sensory processing input to the environment and may cause a sensory overload and exhibit a meltdown. Symptoms are seen in early adolescence when the socialization, speech development and learning; infers limitations in the basic early development. This can be seen early or in later in life in masking the social behavior at a younger age. This disorder is a spectrum and can have intellectual disability's and functioning varies. Higher functioning is identified as Asperger's Syndrome with less limitations in these categories.

Statistics conducted by the Centers for Disease Control, have concluded in 2020 that 1 in 54 children in the United States is diagnosed with Autism Spectrum disorder. In addition, within the statistical analyst, as 1 in 34 boys are concluded being Autistic. 1 in 144 girls are concluded to be Autistic, and IQ with this disorder conclude:

25% have an IQ in borderline range of [71-85]
44% have an IQ of average or above average Another component, are other underling factors associated medical conditions. Percentages from Autism speaks statistics indicate:

31% of have an intellectual disability [>70]
Anxiety disorders 11%~40%
Depression 7% in children. 26% in adults
Schizophrenia 4-35%

With individuals which have Autism, and the limitations on social aspects in early adolescents cause extreme bullying, social isolation, and ridicule. This lack of social efficiency, and the inabilities takes a mental impact and may conclude suicidal ideation; suicide or suicide attempts may occur. According to Sweden's National Patient Registry in a 2015 study found that individuals with Autism are 10 times higher than the average population to commit suicide. This can be concluded with external factors and internal factors for lack of socializations/relationships, nor prevalence in understanding aspects of individual emotional/underlining perceptions. In addition, psychologically in socialization and use of social interaction causes loss of energy after long periods of exposer.

As energy is focused on mimicking and understanding aspects of a given social environment, and non-prevalence of natural instinct/understanding. In Autistic Spectrum Disorder individuals this is harder/easier. May conclude discrimination when acting in social abnormalities which greatly effects in early phycological emotions in adolescence. With the given factors, this effects 6,077,777 million with the given population in the United States in 2019. 13,729,629 million in Europe in possible cases.

Family cost of raising a Child with Autism may cost 1.2 million to 2.4 million depending on the severity, according to a medical journal JAMA Pediatrics. With the 5 average cost of an average child to 230,000-350,000 thousand dollars. In addition, with raising a kid on the spectrum cause sewer stress on a family. With lower support in social spheres, and increase anxiety, depression, and worry. With many physiological factors determine on the severity of the child and the spectrum of disability's causes different psychological components.

Various methods for treating autism have been proposed or implemented. The following is a summary of certain proposed or existing treatment methods.

REFERENCE

"An Exploratory Trial of Transdermal Nicotine for Aggression and Irritability in Adults with Autism Spectrum Disorder."

Findings Include:

"Nicotinic acetylcholine receptors (nAChRs), particularly the α7 nAChR, are implicated in the pathophysiology of both autism spectrum disorder (ASD) and aggressive behavior. We explored the feasibility, tolerability, and preliminary efficacy of targeting nAChRs using transdermal nicotine to reduce aggressive symptoms in adults with ASD. Eight subjects were randomized in a double-blind crossover trial of 7 mg transdermal nicotine or placebo, each for 1 week. Ail participants tolerated nicotine treatment well. Five subjects contributed data to the primary outcome, Aberrant Behavior Checklist-Irritability (ABC-I) subscale change from baseline, which was improved by nicotine compared to placebo. Sleep ratings were also improved by nicotine and correlated with ABC-I improvement. These findings support further investigation of nAChR agonists for aggression and sleep in ASD."

CITATION

Picciotto M R, Lewis A S, Lopez M O, Volkmar F R, Sukhodolsky D G, van Schalkwyk G I. An Exploratory Trial of Transdermal Nicotine for Aggression and Irritability in Adults with Autism Spectrum Disorder. Journal of Autism & Developmental Disorders. 2018; 48(8):2748-2757. doi: 10.1007/s 10803-018-3536-7.

REFERENCE

"Altered nocifensive behavior in animal models of autism spectrum disorder: the role of the nicotinic cholinergic system."

Findings Include:

"Caretakers and clinicians alike have long recognized that individuals with autism spectrum disorder (ASD) can have altered sensory processing, which can contribute to its core symptoms. However, the pathobiology of sensory alterations in ASD is poorly understood. Here we examined nocifensive behavior in ASD mouse models, the BTBR T+Itpr3 tf/J (BTBR) and the fragile-X mental retardation-1 knockout (Fmr1-KO) mice. We also examined the effects of nicotine on nocifensive behavior given that nicotine, a nicotinic cholinergic receptor (nAChR) agonist that has antinociceptive effects, was shown to improve social deficits and decrease repetitive behaviors in BTBR mice. Compared to respective controls, both BTBR and Fmr1-KO had hypo-responsiveness to noxious thermal stimuli and electrical stimulation of C~ sensory fibers, normal responsiveness to electrical stimulation of Aβ- and Aδ-fiber, and hyperresponsiveness to visceral pain after acetic acid intraperitoneal injection. In BTBR, nicotine at lower doses increased, whereas at higher doses, it decreased hotplate latency compared to vehicle. In a significantly different effect pattern, in control mice, nicotine had antinociceptive effects to noxious heat only at the high dose, interestingly, these nocifensive behavior alterations and differential responses to nicotine antinociceptive effects in BTBR mice were associated with significant downregulation of α3, α4, α5, α7, β2, β3, and β4 nAChR subunits in several cerebral regions both, during embryonic development and adulthood. Taken together, these findings further implicate nAChRs in behaviors alterations in the BTBR model and lend support to the hypothesis that nAChRs may be a target for treatment of behavior deficits and sensory dysfunction in ASD."

This study conducted depicts the Nicotinic Cholinergic System in mice with the mutations in nAChR receptors in mice. In addition, Mental retardation for their comparison experiment with a concentration in social defect and compared to sensitivity to outside stimuli. The down regulation of the receptor, and with the exposer of nicotine confirms the target for Autism Spectrum Disorder in behavioral/sensory issues. The targeting the main mutation in sensory processing is tested by thermal response in mice. Which the Mice are being tested in, specifically touch for thermal response pads.

The Study concludes the system of the nicotinic cholinergic system is the point which effects social defects and includes repetitive behavior and which can be showed in "stemming" to calm down sensory processing in Autism spectrum in humans. They found during the mice being treated with a four-week nicotine treatment. In the study it depicts in lower doses the mice with the Social and Autism mutations had more of significant resistance to the Hotplate. Furthermore, an increase in cold plate resistance as in the mice response.

In conclusion of the study, they found because of the nicotine introduced to the mice, the expression of the genes which was affected in the study were more expressed. Specifically, in the nAChR receptors. In the mice with Autism mutations (BTBR) with A5 nAChR concluded attention deficits in the nicotine receptors. Which display a causation of why Autism Spectrum Disorder have an increase chance of ADHD. Nevertheless, the study shows "That altered nAChR submit expression impacts animal behavior, synaptic formation, and neuronal architecture has been shown in investigations of mice with null-mutations of specific nAChR subunits." (Baily et al., 2010) This goes into as the study states that this may not only help the social aspects of Autism Spectrum Disorder but in mice behavior as well.

CITATION

L, Almeida L E F, Nettleton M, et al. Altered nocifensive behavior in animal models of autism spectrum disorder: The role of the nicotinic cholinergic system. Neuropharmacology. 2016, 111:323-334. doi:10.1016/j.neuropharm.2016.09.013.

REFERENCE

"Cotinine: Beyond that Expected, More than a Biomarker of Tobacco Consumption"

Findings include: "A greater incidence of tobacco consumption occurs among individuals with psychiatric conditions including post-traumatic stress disorder (PTSD), bipolar disorder, major depression, and schizophrenia, compared with the general population. Even when still controversial, it has been postulated that smoking is a form of self-medication that reduces psychiatric symptoms among individuals with these disorders. To better understand the component(s) of tobacco-inducing smoking behavior, greater attention has been directed toward nicotine. However, in recent years, new evidence has shown that cotinine, the main metabolite of nicotine, exhibits beneficial effects over psychiatric symptoms and may therefore promote smoking within this population. Some of the behavioral effects of cotinine compared to nicotine are discussed here. Cotinine, which accumulates in the body as a result of tobacco exposure, crosses the blood-brain barrier and has different pharmacological properties compared with nicotine. Cotinine has a longer plasma half-life than nicotine and showed no addictive or cardiovascular effects in humans. In addition, at the preclinical level, cotinine facilitated the extinction of fear memory and anxiety after fear conditioning, improved working memory in a mouse model of Alzheimer's disease (AD) and in a monkey model of schizophrenia. Altogether, the new evidence suggests that the pharmacological and behavioral effects of cotinine may play a key role in promoting tobacco smoking in individuals that suffer from psychiatric conditions and represents a new potential therapeutic agent against psychiatric conditions such as AD and PTSD."

CITATION

Moran, Valentina Echeverria. "Cotinine: Beyond that Expected, More than a Biomarker of Tobacco Consumption." Frontiers in pharmacology vol. 3 173. 10 Oct. 2012, doi: 10.3389/fphar.2012.00173.

Any discussion of documents, acts, materials, devices, articles, or the like, which has been included in the present specification is not to be taken as an admission that any or ail of these matters form part of the prior art base or were common general knowledge in the field relevant to the present disclosure as it existed before the priority date of each claim of this application.

SUMMARY OF THE INVENTION

This summary is provided to introduce a variety of concepts in a simplified form that is disclosed further in the detailed description of the embodiments. This summary is not intended to identify key or essential inventive concepts of the claimed subject matter, nor is it intended for determining the scope of the claimed subject matter.

The embodiments provided herein relate to a pharmaceutical drug therapy for autism is disclosed, including a sufficient amount of nicotine and a sufficient amount of amphetamine.

Unfortunately, there is not currently exist an effective pharmaceutical drug therapy for the treatment of autism. In order to solve these and other shortcomings of known systems, methods, or therapies for treating autism, in various exemplary, non-limiting embodiments, the pharmaceutical drug therapy for autism of the present disclosure provides a pharmaceutical drug therapy for autism, comprising Non-ionized Nicotine C10H14N2; and Amphetamine C9H13N.

In various exemplary, non-limiting embodiments, the Nicotine is in said form of droplets. The droplets aid some individuals who may be sensitive or have an aversion to touch, patches, pills, textures, etc. In such, providing the nicotine in the form of a droplet aid in increasing compliance with the therapy.

In various exemplary, non-limiting embodiments, the Nicotine has a pH value of 3.0. Nicotine is safer if congested and the negative side effects decline largely, and the inhalants of chemicals would not be well for adolescence. Smoking the Nicotine alkaloid, causes inhaling of carbon which goes into the lungs and prevents oxygenation to the brain. Increase a possibility of schizophrenia when smoked form of the plant-based alkaloid. Same chances of schizophrenia when Marijuana is vaporized and smoked but not digested. The chemical of Cotinine C10H12N2O is released and is not harmful. But the Cotinine reaches a plateau and does not affect the body. Cotinine is produced when the body metabolizes Nicotine and can be digested and not inhaled. It has benefits of the side effects which the study concludes which can help Autism Spectrum Disorder. The Anxiety, depression, and may help schizophrenia which effects 4-35% of the individuals who are affected with Autism Spectrum Disorder.

In some embodiments, the Nicotine as provided in the composition disclosed herein has a pH value between 2-8.

The present disclosure separately and optionally provides a pharmaceutical drug therapy for autism that utilizes non-ionized Nicotine and Amphetamine. These and other aspects, features, and advantages of the present disclosure are described in or are apparent from the following detailed description of the exemplary, non-limiting embodiments of the present disclosure and the accompanying FIGURES. Other aspects and features of embodiments of the present disclosure will become apparent to those of ordinary skill in the art upon reviewing the following description of specific, exemplary embodiments of the present disclosure in concert with the FIGURES.

BRIEF DESCRIPTION OF THE DRAWINGS

A more complete understanding of the embodiments, and the attendant advantages and features thereof, will be more readily understood by references to the following detailed description when considered in conjunction with the accompanying drawings wherein:

FIG. 1 illustrates a synthesized chemical 2-D structure of 1-[2-(1-methylpyrrolidin-2-yl)phenyl]propan-2-amine, according to some embodiments.

DETAILED DESCRIPTION

For simplicity and clarification, the compounds and principles of the pharmaceutical drug therapy for autism according to the present disclosure are explained with reference to various exemplary embodiments of a pharmaceutical drug therapy for autism according to the present disclosure. The basic explanation of the compounds and principles of the pharmaceutical drug therapy for autism is applicable for the understanding, synthesis, and implementation of the pharmaceutical drug therapy for autism of the present disclosure. It should be appreciated that the pharmaceutical drug therapy for autism can be adapted to many applications where a pharmaceutical drug therapy for autism can be utilized.

As used herein, the word "may" is meant, to convey a permissive sense (i.e., meaning "having the potential to"), rather than a mandatory sense (i.e., meaning "must"). Throughout this application, the terms "comprise" (and any form of comprise, such as "comprises" and "comprising"), "have" (and any form of have, such as "has" and "having"), "include", (and any form of include, such as "includes" and "including") and "contain" (and any form of contain, such as "contains" and "containing") are used as open-ended linking verbs. It will be understood that these terms are meant to imply the inclusion of a stated element, integer, step, or group of elements, integers, or steps, but not the exclusion of any other element, integer, step, or group of elements, integers, or steps. As a result, a system, method, or apparatus that "comprises", "has", "includes", or "contains" one or more elements possesses those one or more elements but is not limited to possessing only those one or more elements. Similarly, a method or process that "comprises", "has", "includes" or "contains" one or more operations possesses those one or more operations but is not limited to possessing only those one or more operations.

It should also be appreciated that the terms "pharmaceutical", "drug", and "drug therapy" are used for basic explanation and understanding of the compounds, systems, and methods of the present disclosure. Therefore, the terms "pharmaceutical", "drug", and "drag therapy" are not to be construed as limiting the compounds, systems, and methods of the present disclosure.

For simplicity and clarification, the pharmaceutical drug therapy for autism of the present disclosure will be referenced and/or described as being utilized in the treatment of autism. It should be appreciated that these are merely exemplary utilizations of the pharmaceutical drug therapy for autism and are not to be construed as limiting the present disclosure. Thus, the pharmaceutical drug therapy for autism of the present disclosure may ultimately be used as a treatment for autism or other ailments or maladies.

Turning now to the appended drawing FIGURE(s), FIG. 1 illustrates an exemplary embodiment of a synthesized chemical 2D structure of a pharmaceutical drag therapy for autism, according to the presently disclosed compounds, systems, and/or methods.

In certain illustrative, non-limiting embodiment(s) of the presently disclosed compounds, systems, and/or methods, the pharmaceutical drag therapy for autism comprises components that are synthesized as an extended release tablet over an 8-hour-12-hour period and involving doses of Non-Ionized Nicotine C10H14N2 and Amphetamine C9H13N.

These compounds would synthesize and would dispense a ratio of each compound per hour in order to have a continued effect on the brain. In various exemplary, non-limiting embodiments) the synthesized chemical 2D structure is as illustrated in FIG. 1. In various exemplary, non-limiting embodiment(s) the ratio is:

Ionized Nicotine C10H14N2 and Amphetamine C9H13N
Amphetamine C9H13N

Once synthesized, this exemplary embodiment of the pharmaceutical drug therapy for autism would be provided in dosages as follows:

Adolescences 13-16 5 mg 1-Amphetamine
16-18 10 mg 1-Amphetamine

Extended Release:
Extended over 8 to 12 hours
Ionized Nicotine C10H14N2. PH 3.0

Once synthesized, this exemplary embodiment of the pharmaceutical drug therapy for autism would be provided in dosages as follows:

Adolescences 13-16 2 mg ionized Nicotine
16-18 4 mg ionized Nicotine Per 2 hours
Adult 18<4 mg ionized Nicotine Extended Release:
13-16 12 mg ionized Nicotine 16-18 20 mg ionized Nicotine
18<20 mg ionized Nicotine
Adult 18<10 mg 1-Amphetamine
8-hour Extended release Once synthesized, this exemplars' embodiment of the pharmaceutical drug therapy for autism would be provided in dosages as follows:

Adolescences
13-16 8 mg ionized Nicotine
16-18 15 mg ionized Nicotine

Extended Release:
12-hour Extended release

Once synthesized, this exemplary embodiment of the pharmaceutical drug therapy for autism would be provided in dosages as follows:

Adult
Adolescences Adult
18<15 mg ionized Nicotine
13-16 8 mg ionized Nicotine 16-18 15 mg ionized Nicotine
ionized Nicotine C10H14N2

The Non-ionized Nicotine used is from burning Flue cured tobacco and distilled from the smoke. The process continues until the Nicotine droplets have a PH value of 3.0. This would enable slower metabolism, and longer effect over a period of time. The effects in the blood stream for 2 hours, and concentration in the brain.

In some embodiments, the droplets aid some individuals who may be sensitive or have an aversion to touch, patches, pills, textures, etc. In such, providing the nicotine in the form of a droplet aid in increasing compliance with the therapy.

The causes of Autism vary, the main symptoms of social and cognition function can be contributed to the neuro-brain structure. The Neurexin-1 beta gene mutations and cause a shortage in the prefrontal and orbital part, which causes anti-social activities; contributes to Autism, Anti-social Disorder, and social anxiety.

Neurexins exhibit inhibitory and excitatory in the peripheral/central nervous system in the control of body functions in the synapses. The Neurexins bind to other neurons with a protein exchange and is important for connections to neurons.

The acetylcholine receptor is located within somatic nervous system in the role of connecting different portions and in the communication network. Autism Spectrum Disorder shortage is impacted by the lack of B-Neurexin 1 proteins which the gene produces. The mutations in the Neurexins in an Autistic individual's brain causes the shortage and causes the social limitations in brain functionality. The mutations cause art imbalance and disrupts circuit development and is a major impact of Autism Developmental Disorder.

B-Neurexin 1 is very important in attracting proteins for synaptic and circuit development. B-Neurexin 1 have an affinity to Nicotine binding and re-configure the synaptic circuits of the mutations. A point of configuration of these Nicotine receptors to the Limbic system, Dorsolateral Striatum and the major influence of the orbital prefrontal cortex in the hippocampus. IQ Sec 2 mutation and an addition of nicotine binding in the hippocampus would effect of the emotional response for large improvement. Nicotine binding in this area of influence of the hippocampus, in turn with the Diencephalon/Nucleus reunions. Would input to the hippocampus in the social aspects of the brain. In addition, Dentate Gyrus in Dorsal ventral hippocampus amplifies signals front Entorhinal cortex. The Dentate gyrus controls reading new environments and creating a memory in representation of environments detail/sensation. The Entorhinal Cortex is receiving stimulus of the environment.

Furthermore, Entorhinal cortex promotes transfer and memory/storage of information. This is another main point of interest in Autism Spectrum Disorder, this conveys emotional information which is limited in an Autistic individual. Furthermore, Neuroligin binds to the receptors and, reinforce with the implication of Nicotine then focuses on the damage and normalization of the complex. MDMA receptors bind with the extra neurexins and makes it transient. This extra serotine helps sleep patterns with Nicotine and helps balance and depressive effects. Without this, it goes into the long-term depression with the mutations and can correlate the data of the suicide rate/depression rate among individuals on the autism spectrum. In addition, effects on memory and learning social aspects of the variables which make it difficult to interact. These mutated nicotine receptors prevent AMPH receptors which cause associated disabilities in behavior and learning which come with this disorder. AMPH Receptors are responsible of dopamine transaction which is a characteristics of Nicotine binding.

The Nicotine helps the Gabba Receptor in inhibitory neurons and in contrast affects the TRN and concludes another aspect of the reason of the Autism Spectrum Disorder in sensory processing. Gabba Receptor which is an inhibitory neuron. The Autism mutation limits TRN cortex handling, and mutations cause sensory overloads because of lack of regulation of the processing in an individual which has the disorder. This exhibit's and the abnormality in regulation and process in limitations in synaptic genesis, and electrical confinement of chemical neurons.

TRN is placed under the cortex and connects to the Basel Forebrain afferents in visual neurons. In the Basel Forebrain, the Nicotine would bind to the a-7nAChR of B2, for the function in memory, and learning and concentration. With the improvement of the neuro connections by the Nicotine receptors and correlates improvements in a decline in aggression involving sensory regulation seen in Autism Spectrum Disorder. Studies conducted with Nicotine therapies point to a decrease in Schizophrenia and Dementia, with the nAChR agonist acting as a limitation for the volume of aggression. Another Aspect of the implication of Nicotine is the anti-depression effects, and some factors which release serotonin/noradrenaline. This uptake in the release of serotonin helps with sleep cycles and anti-depression. This would help and increase effectiveness of other anti-depression medication. This would in turn help 26% of the Autism population, and 7% percent of children. Commonly, individuals with Autism feel depressive symptoms at some point in finding relationships and the isolation from other individual may help with the emotion disparity. This is another reaction because of the nAChR activation of Nicotine binding.

In the Pharmaceutical treatment, the other component is Amphetamine and corresponds with the blocking of dopamine in the Nicotine component. Nicotine expels dopamine which may cause addiction and Amphetamine decease dopamine receptors. They decrease Nicotine caused dopamine, with the implication of neurexin-1 gene. As the Amphetamine blocks/lessens dopamine regulation. The Amphetamine effects the Dorsolateral Striatum and change the response when doing a certain task and releases dopamine. Amphetamine blocks the Kappa-opioid receptors which regulates addiction. The Amphetamine regulates the Kappa-opioid receptors, and block/turn back to normal function.

This reduces the pleasure and blocks causation of addiction of dopamine in the individual. With Amphetamine to counter the Nicotine and can be implemented to a younger age group without the implication of a dependency. This also targets the mRNA of the D2 dopamine receptors level in the Amygdala and the Basal Amygdala.

The Basel Amygdala is responsible for the stimuli which may enact a fear response and is activated in withdraw from a certain substance. Which these receptors that counters the Nicotine in reactions to the dopamine response but keeps the B-Neurexin 1 proteins job to help the deficiencies with the implication of the Autism Spectrum Disorder.

Amphetamine when involved with Autism spectrum disorder which have receive Amphetamine would amplify brain activity. With the 31% which have an intellectual disability [>70], and average to above Average intellect. This would increase locomotive function and neuroplasticity would help the new neuron connections with the Amphetamine. This can help the individuals with Autism Spectrum disorder and be able to cooperate better in society. In addition, make a better stable connection in order to further and help in later life.

While the present disclosure has been described in conjunction with the exemplary embodiments outlined above, the foregoing description of exemplary embodiments of the present disclosure, as set forth above, are intended to be illustrative, not limiting and the fundamental disclosed compounds, systems, and/or methods should not be considered to be necessarily so constrained. It is evident that the present, disclosure is not limited to the particular variation set forth and many alternatives, adaptations modifications, and/or variations will be apparent to those skilled in the art.

Trial:
  Autism score of the Adult Autism Scale: 78 needed for significance/scored 154
    Age: 18
    Other disabilities: Dysgraphia. Dyslexia, ADHD, ADD and General Anxiety Disorder Description:
  Trouble with analyzing social environment socially isolated, and doesn't understand social environments. Described as unpopular and could not hold relationships and holds a "Face Mask" and is embarrassed to be the induvial that he sees himself.

Control:
  Self-description before compound in the aspect of the individual's life before-exposer and varies of trouble in the induvial life that they want to report.

Trial: 1
Control:
  "Difficulties involve socially outcasted and mainly focusing on my studies. I can't focus on class with ail of the sounds from the teachers and classmates. I couldn't make eye contact for a long period of time without a pain in the back of my head. In high school by lunch I am exhausted from trying to read people when they talk to me in class and between periods. I normally have to eat lunch by myself in order to recharge. 1 am completely lost in social situations and didn't, understand social groups and copied some of the "popular kids" actions which felt wrong because it wasn't myself. When I did that, I didn't feel who I was, and it made me more sensory "sensitive." I was very social at the beginning of school but kind of fell apart, at last period counting down the clock until I could leave When I get home, I am usually so exhausted and slept until dinner, and sometimes after that. That I guess, messed up sleeping schedule because I usually start homework at 10 pm, and with my other learning disabilities it takes on average 4 hours to do 1-2 hours of homework. This took a mental tool through the week constantly exhausted and start getting some depressive symptoms. Then by the weekend I sleep until 2 pm-3 pm every day, and then hang with my few good friends which I could be myself around. Some nights I try to get back on a schedule but sometimes I can't sleep even though 1 am exhausted. I knew my friends since when I was young, so they were used to me and vice-versa. It didn't take a toll as normal interaction at school, but I worked on the weekend to support my family which adds additional anxiety. I read some psychological books to help me out, so I try to keep a balance and I still come up short, in a lot of areas. It was easy in middle school for social interaction, in Elementary school I could just smile, and everyone could like me. But in middle school, all I had to do was not to talk and focus on schoolwork. I still got bullied but didn't understand sarcasm, so it didn't bother me, until I figured it out in high school. In high school, I found out I could interact with individuals by tutoring and doing projects. But came to the same problem as mentioned. But with more of a workload and trying sports, so I can understand how socialize more. This created a spiral and affected me emotionally and with the extra anxiety with college applications.

Experimentation:
  Date: Oct. 13, 2017
Description:
  The individual would take 20 mg of Amphetamine once a day with an extended release tablet for 12 hours. With one nicotine gum 4 milligram every hour for a 10-hour period, and this will be daily usage over a month period of time.

After a Month of Use:
  "On the first day, improvements were noted and increase in relaxation when talking with individuals. I have noticed that my sensor perception was better and made my day at school less uncomfortable. Sounds did not bother me as much and I felt more in touch with the atmosphere in class. The clicking of the pens and the screeching of the chairs started to not bother me, and I felt in more control of my thought process. I could focus on my teacher more without the slight disturbances. As the week goes on the social connecting was improved and I could understand and focus on individuals' social aspects. I could connect and make eye contact for longer periods of time and individuality in understanding socially came about. I started, to understand body language and could make conversations easier surprisingly. I could understand more unspoken social cues and could categorize more of what is socially acceptable. In the social circles at my high school and increased my social standing with the other groups. I found humor more easily identifiable and copying to induce more social cohesion. It is noted that after the experimentation, the individual had a major decrease in the adult autism scale.

Stemming was declining, as for me is moving back in forth in my chair. My parents and my two friends saw a difference in my acting in a more positive light. I was apparently more "easy going." I still had my very analytical thought pattern but moved towards the different emotional concepts of relationships. But seemed the analytical thought didn't matter as much for talking with a neo-typical. It did help when analyzing, and my sensory overloads declined as well but still happened on special occasions.

Focusing on certain subjects and my thought processes were more decisive and made a major difference. Usual outcome is that my brain is scattered with the never-ending ideas, or "20 Tabs open all at once." I found that I did not get tired after little social conducts and trying to figure out social constructs/keeping my perception. Usually after a day at school, I come home and would get extremely tired after interacting all day. But I had more energy and could knock out homework more efficiently. I could hangout after school with friends and would not be as tired because of the extra energy. This improved my social life at school, and improved social stance with my grade. I had the sense of being normal and accepted. I have noticed that my sleeping pattern was better and didn't go bed at 2 in the morning as I do on some nights. If given the option I would take this every day, as in order to better my life and increase social aspects of my life." Accordingly, the present disclosure separately and optionally provides an effective treatment for autism that, comprises pharmaceutical drug therapy.

Furthermore, where a range of values is provided, it is understood that every intervening value, between the upper and lower limit of that range and any other stated or intervening value in that stated range is encompassed within the present disclosure. The upper and lower limits of these smaller ranges may independently be included in the smaller ranges and is also encompassed within the present disclosure, subject to any specifically excluded limit in the stated range. Where the stated range includes one or both of the limits, ranges excluding either or both of those included limits are also included in the present disclosure.

It is to be understood that the phraseology of terminology employed herein is for the purpose of description and not of limitation. Unless defined otherwise, all technical and scientific terms used herein have the same meaning as commonly understood by one of ordinary skill in the art to which the present disclosure belongs.

In addition, it is contemplated that any optional feature of the inventive variations described herein may be set forth and claimed independently, or in combination with any one or more of the features described herein.

Accordingly, the foregoing description of exemplary embodiments will reveal the general nature of the present disclosure, such that others may, by applying current knowledge, change, vary, modify, and/or adapt these exemplary, non-limiting embodiments for various applications without departing from the spirit and scope of the present disclosure and elements or methods similar or equivalent to those described herein can be used in practicing the present disclosure. Any and ail such changes, variations, modifications, and/or adaptations should and are intended to be comprehended within the meaning and range of equivalents of the disclosed exemplary embodiments and may be substituted without departing from the true spirit and scope of the present disclosure.

Also, it is noted that as used herein and in the appended claims, the singular forms "a", "and", "said", and "the" include plural referents unless the context clearly dictates otherwise. Conversely, it is contemplated that the claims may be so-drafted to require singular elements or exclude any optional element indicated to be so here in the text or drawings. This statement is intended to serve as antecedent basis for use of such exclusive terminology as "solely", "only", and the like in connection with the recitation of claim elements or the use of a "negative" claim limitation(s).

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shah support claims to any such combination or subcombination.

It will be appreciated by persons skilled in the art, that the present embodiment, is not limited to what has been particularly shown and described hereinabove. A variety of modifications and variations are possible in light of the above teachings without departing from the following claims.

What is claimed is:

1. A pharmaceutical drug therapy for autism, comprising:
   a sufficient amount of nicotine; and
   a sufficient amount of amphetamine,
   wherein the sufficient amount of nicotine and the sufficient amount of amphetamine are administered to a human; and
   wherein the sufficient amount of nicotine is provided in the form of droplets.

2. The pharmaceutical drug therapy of claim 1, wherein the sufficient amount of nicotine is formulated having a pH value of between 2.0 and 8.0.

3. The pharmaceutical drug therapy of claim 2, wherein the sufficient amount of nicotine is formulated having a pH value of about 3.0.

4. The pharmaceutical drug therapy of claim 1, wherein the sufficient amount of nicotine is at least partially comprised of non-ionized nicotine.

5. The pharmaceutical drug therapy of claim 1, wherein the amphetamine is 1-amphetamine.

6. The pharmaceutical drug therapy of claim 1, wherein the amphetamine is combined with 1-[2-(1-methylpyrrolidin-2-yl)phenyl]propan-2-amine.

7. A pharmaceutical drug therapy for autism, comprising:
   between 2-20 mg of nicotine; and
   between 2-25 mg of amphetamine,
   wherein the nicotine and the amphetamine are administered to a human;
   wherein the sufficient amount of nicotine is provided in the form of droplets;
   wherein the nicotine is formulated having a pH value of between 2.0 and 8.0;
   wherein the nicotine is at least partially comprised of non-ionized nicotine; and
   wherein the amphetamine is 1-amphetamine provided to an adult in the amount of between 10-15 mg per day.

8. The pharmaceutical drug therapy of claim 7, wherein the amphetamine is combined with 1-[2-(1-methylpyrrolidin-2-yl)phenyl]propan-2-amine.

9. The pharmaceutical drug therapy of claim 7, wherein the l-amphetamine is provided to an adolescent in the amount of between 2-15 mg per day.

10. The pharmaceutical drug therapy of claim 7, wherein the l-amphetamine is provided in an extended-release tablet.

11. A pharmaceutical drug therapy for autism, comprising:
between 2-20 mg per day of ionized nicotine; and
between 2-25 mg per day of l-amphetamine provided in an extended-release form;
wherein the nicotine and the amphetamine are administered to a human, and
wherein the sufficient amount of nicotine is provided in the form of droplets.

* * * * *